US008161816B2

(12) United States Patent
Beck

(10) Patent No.: US 8,161,816 B2
(45) Date of Patent: Apr. 24, 2012

(54) HEARING TEST METHOD AND APPARATUS

(76) Inventor: Matthew Beck, Glendale Heights, IL (US)

( * ) Notice: Subject to any disclaimer, the term of this patent is extended or adjusted under 35 U.S.C. 154(b) by 359 days.

(21) Appl. No.: 12/611,304

(22) Filed: Nov. 3, 2009

(65) Prior Publication Data

US 2011/0100127 A1    May 5, 2011

(51) Int. Cl.
*A61B 5/12* (2006.01)
*H04R 29/00* (2006.01)

(52) U.S. Cl. .......................................... 73/585; 381/60
(58) Field of Classification Search ............... 73/585; 381/60, 57, 58, 312, 314, 323
See application file for complete search history.

(56) References Cited

U.S. PATENT DOCUMENTS

| 5,239,872 | A |   | 8/1993  | Meyer-Bisch |         |
|-----------|---|---|---------|-------------|---------|
| 5,402,494 | A | * | 3/1995  | Flippe et al. | 381/314 |
| 5,928,160 | A |   | 7/1999  | Clark et al. |         |
| 6,379,314 | B1 |   | 4/2002  | Horn |         |
| 6,447,461 | B1 |   | 9/2002  | Eldon |         |
| 6,658,172 | B1 | * | 12/2003 | Scobey et al. | 385/15 |
| 6,840,908 | B2 |   | 1/2005  | Edwards et al. |         |
| 7,016,504 | B1 |   | 3/2006  | Shennib |         |
| 7,106,870 | B2 | * | 9/2006  | Meier et al. | 381/314 |
| 7,288,072 | B2 | * | 10/2007 | Stott et al. | 600/559 |
| 7,366,315 | B2 | * | 4/2008  | Blamey et al. | 381/312 |
| 7,978,868 | B2 | * | 7/2011  | Blamey et al. | 381/312 |
| 8,045,737 | B2 | * | 10/2011 | Stirnemann | 381/318 |
| 2003/0065276 | A1 |   | 4/2003  | Akita |         |
| 2003/0072455 | A1 | * | 4/2003  | Johansen et al. | 381/60 |
| 2003/0073927 | A1 | * | 4/2003  | Johansen et al. | 600/559 |
| 2003/0078515 | A1 |   | 4/2003  | Menzel et al. |         |
| 2006/0210090 | A1 |   | 9/2006  | Shennib |         |

* cited by examiner

*Primary Examiner* — J M Saint Surin
(74) *Attorney, Agent, or Firm* — David J. Bremer

(57) ABSTRACT

A method and apparatus for administering a hearing test that emits a test sound with changing volume with respect to elapsed time. The volume changes according to a pre-determined relationship between the volume and elapsed time. The hearing test utilizes the elapsed time until a subject signals the test sound is audible, and the pre-determined relationship, to determine the subject sound pressure level threshold for the test sound.

20 Claims, 4 Drawing Sheets

HEARING TEST METHOD AND APPARATUS

The invention is a hearing test method that can be self-administered and can produce highly accurate results, and apparatus practicing the hearing test method. The hearing test method can utilize a test sound with varying volume, where the volume varies with elapsed time according to a pre-determined relationship.

Some conventional hearing tests emit consecutive sounds, each at different volumes, the sounds separated by intervals of silence. Subjects respond after each emitted sound to indicate audibility and the volume of the audible sound is noted. Such tests can result in false readings due to subject anticipation of the sequence and due to other causes not related to audibility.

Other tests use simultaneous sounds having different frequencies. Such tests can result in false readings due to cultural and personal preferences favoring certain chordal arrangements over others.

The hearing test method of the invention can generate a test sound at a volume that varies with time according to a pre-determined relationship. The hearing test method can measure elapsed time from the start of the test sound until the subject indicates audibility. The elapsed time can be applied in accordance with the pre-determined relationship to determine a sound pressure level (SPL) at which the subject indicates audibility.

The hearing test method applies the elapsed time to the pre-determined relationship to calculate a corresponding SPL. The pre-determined relationship can be a direct relationship, can be a linear relationship, can be an discontinuously-varying relationship, and can be various other relationships so long is the relationship is known and can be used to calculate a distinct sound pressure level for each different elapsed time.

The hearing test method can also include a calibration procedure for identifying differences between sound generating systems and can compensate for the identified differences to produce accurate results in spite of system-specific sound generating characteristics.

BRIEF SUMMARY

An embodiment of the invention includes a hearing test method comprising reading a pre-generated, read-only, test file via a computer processor from a test file storage location, the test file comprising computer-executable test instructions for causing a sound generating system to generate a continuous test sound at changing test volume amplitude where the test volume amplitude changes according to a pre-defined relationship between the test volume amplitude and elapsed time, the test sound being a single tone at a single audible frequency; executing the computer-executable test instructions via the computer processor and causing the sound generating system to generate the test sound; detecting, via the computer processor, a subject signal that indicates test sound audibility; measuring, via the computer processor, a test elapsed time from executing the test instructions until detecting the subject signal; transforming the test elapsed time, via the computer processor, into a subject sound pressure level threshold at the single audible frequency using the pre-defined direct relationship between the test volume amplitude and the test elapsed time; and displaying the subject sound pressure level threshold via a graphic display device.

An alternate embodiment of the invention includes a hearing test method comprising a calibration procedure comprising: reading a pre-generated, read-only, calibration file from a calibration file storage location, the calibration file comprising computer-executable calibration instructions for causing a sound generating system to generate a calibration sound at a constant calibration volume amplitude, the calibration sound being a single tone at a single audible frequency; the calibration procedure further comprising executing the calibration instructions via a computer processor to cause the sound generating system to generate the calibration sound; measuring with an independent sound pressure level meter an actual sound pressure level of the calibration sound generated by the sound generating system; measuring a difference between the actual sound pressure level of the calibration sound and a predetermined target sound pressure level; storing a calibration number in a calibration number storage location, where the calibration number is related to the difference between the actual sound pressure level generated by the sound generating system and the predetermined target sound pressure level, the hearing test method further comprising a test procedure comprising: reading a pre-generated, read-only, test file from a test file storage location, the test file comprising computer-executable test instructions for causing the sound generating system to generate a continuous test sound at increasing test volume amplitude where the test volume amplitude increases according to a pre-defined direct relationship between the test volume amplitude and elapsed time, the test sound being a single tone at the single audible frequency; the test procedure further comprising reading the calibration number from the calibration number storage location; adjusting a sound generating system volume setting in accordance with the calibration number to compensate for the measured difference between the actual sound pressure level generated by the sound generating system and the predetermined target sound pressure level; executing the test instructions via a computer processor to cause the sound generating system to generate the test sound; detecting, via the computer processor, a subject signal that indicates test sound audibility; measuring, via the computer processor, a test elapsed time while executing the test instructions until detecting the subject signal; transforming the test elapsed time via the computer processor into a subject sound pressure level threshold at the single audible frequency using the pre-defined direct relationship between the test volume amplitude and the test elapsed time; and the hearing test method further comprising an output procedure comprising displaying the subject sound pressure level threshold via a graphic display.

Another embodiment of the invention includes a computer program product comprising: at least one computer-readable medium comprising computer-executable program code embodied therein, the program code when executed providing a method for administering a hearing test, the method comprising: a test procedure comprising: reading a pre-generated, read-only, test file from a test file storage location, the test file comprising: computer-executable test instructions for causing a sound generating system to generate a continuous test sound at increasing test volume amplitude where the test volume amplitude increases according to a pre-defined direct relationship between the test volume amplitude and elapsed time, the test sound being a single tone at the single audible frequency; executing the test instructions and causing the sound generating system to generate the test sound; detecting a subject signal where the subject signal indicates test sound audibility; measuring a test elapsed time from executing the test instructions until detecting the subject signal; transforming the test elapsed time into a subject sound pressure level threshold at the single audible frequency by applying the pre-defined direct relationship between the test volume amplitude and the test elapsed time; and the method further comprising an output procedure comprising: displaying the subject sound pressure level threshold on a graphic display device.

DRAWINGS

FIG. 1 a diagram showing a hearing test method embodiment of the invention.

DETAILED DESCRIPTION

The hearing test method 10 can be implemented via a computer processor 11 to process method steps. The processor 11 can execute instructions that are resident in central processing unit (CPU) memory to process method steps, can read instructions from various storage locations and execute the instructions, and can accept instructions input by a user and execute the instructions. The processor 11 can output instructions to, and can input instructions from, a sound generating system, a data storage device, a graphic display, a graphic user interface, and various peripheral devices and systems, in order to process method steps.

The hearing test method 10 can be self-administered by a first user to evaluate hearing, where the first user can act as a tester and as a subject 80. The hearing test method 10 can be administered to a first user by a second user, where the second user can act as the tester and the first user can act as the subject 80. In an embodiment, the subject 80 can be proximal a sound generating system 121 so as to hear a test sound generated by a sound generating system 121. The subject 80 can indicate test sound audibility by generating a subject signal.

Figure 1:
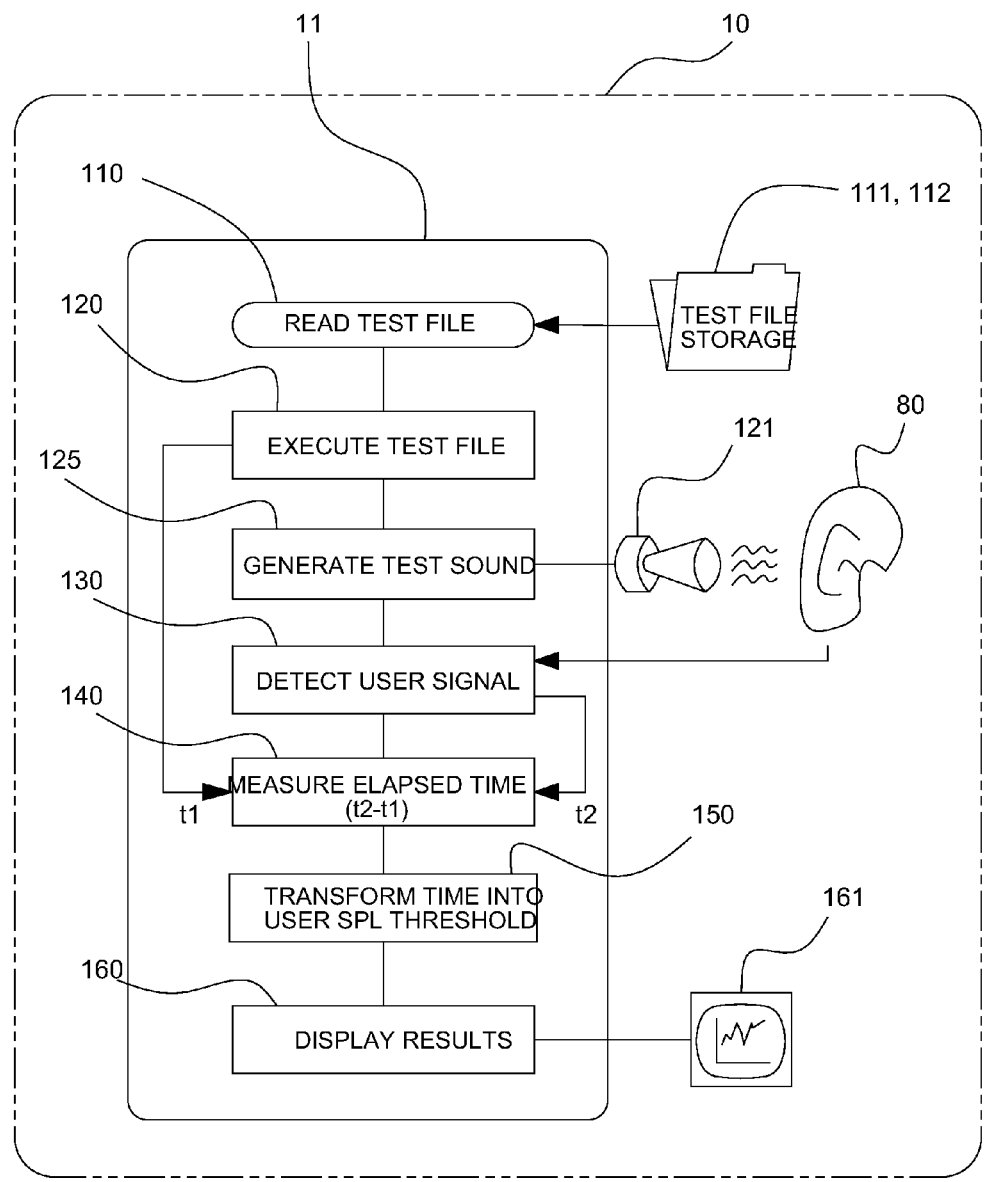
Figure 2:
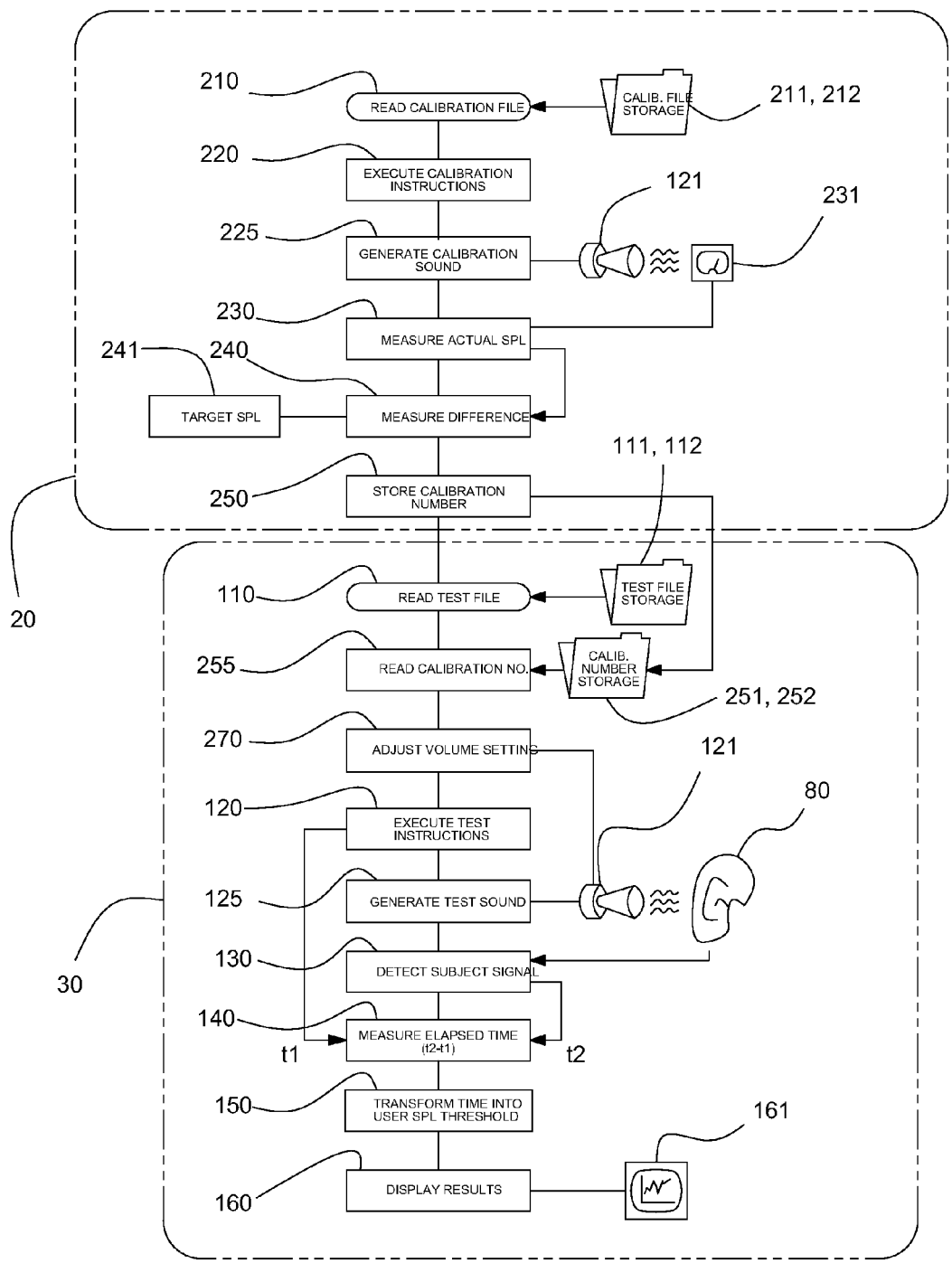
FIG. 2 is a diagram showing a different hearing test method embodiment including a test procedure and a calibration procedure.

As shown in FIG. 1, the hearing test method 10 via the computer processor 11 can obtain instructions for generating a test sound by reading 110 a pre-generated test file 111 from a test file storage location 112. The test file storage location 112 can be a computer-readable medium such as a compact disk, a floppy disk, and a tape drive. The test file storage location 112 can be a hard disk drive, and can be a flash drive. The test file storage location 112 can be various volatile and non-volatile memory locations.

The test file storage location 112 can be accessed over a computer network including a wireless network and the Internet.

The test file 111 can comprise instructions for causing the sound generating system to generate a test sound. The test file 111 can be pre-generated independently and remotely, and can be read-only protected and otherwise protected so that the instructions for generating the test sound are unvarying when used for subsequent tests and when used with various sound generating systems.

The test sound can comprise a single tone at a single audible frequency. The test sound can have changing test volume amplitude. The test volume amplitude can change according to a pre-defined relationship between the test volume amplitude and elapsed time. "Volume amplitude" as used here and throughout, is defined as a theoretical sound pressure level produced by a non-specific sound generating system upon receiving computer-executable instructions to generate a sound at the volume amplitude. An actual sound pressure level produced by the sound generating system receiving the computer-executable instructions can vary from the theoretical sound pressure level designated by the volume amplitude.

The actual sound pressure level produced by the sound generating system 121 upon receiving the computer executable instructions can be considered approximately equal to the volume amplitude specified by the instructions. Alternatively, the actual sound pressure level can be approximated by transposing the volume amplitude up and down volume-wise according to sound generating system-specific guidelines. Alternatively, the actual sound pressure level can be approximated by utilizing a calibration procedure to evaluate characteristics of the sound generating system.

The test sound can be a continuous test sound with increasing test volume amplitude where the test volume amplitude increases with elapsed time according to the pre-defined relationship between the test volume amplitude and elapsed time. The test volume amplitude can increase according to a direct relationship between test volume and elapsed time, and can increase according to a direct linear relationship between test volume and elapsed time.

The test file 111 can comprise an audio file for storing an audio bit stream. The test file can comprise a raw bit stream. The test file 111 can comprise a compressed .wav file and can comprise an uncompressed .wav file. The test file 111 can comprise various audio formats such as AIFF, AU, and PCM, as well as other standard formats and custom formats, so long as the test file 111 can be executed and thus cause the sound generating system to produce the test sound.

The hearing test method 10 can further comprise executing 120 the test instructions via the computer processor 11 and causing the sound generating system 121 to generate 125 the test sound. The computer processor 11 can execute the test instructions by serially reading and executing the instructions from the test file storage location 112. Alternatively, the computer processor 11 can read the instructions into CPU memory and execute them. The computer processor 11 can read instructions for generating the test sound from the test file storage location 112 and can read instructions relating to the pre-defined direct relationship between test volume amplitude and elapsed time into CPU memory. The computer processor 11 can read instructions via various modes and methods and can store instructions in various locations for subsequent execution.

The computer processor 11 can be part of a general-purpose computer. The computer processor 11 can be converted to a special-use processor by reading instructions into CPU memory and thus organizing the processor 11 into a hearing test method processor.

The sound generating system 121 can comprise a sound transducer and a computer audio card for facilitating output of audio signals to the sound transducer. Alternatively, the sound generating system 121 can comprise various components, expansion cards, USB sound cards, audio interfaces, and combinations thereof for outputting signals to the sound transducer. The sound generating system 121 can comprise software interacting with various sound generating system components to facilitate outputting signals to the sound transducer.

The sound transducer can comprise a speaker for generating the test sound. The speaker can be a conventional electroacoustical transducer such as a moving-coil speaker. Alternatively, the speaker can be a piezoelectric, electrostatic, ribbon, bending wave, and various other speaker designs and combinations thereof, so long as the speaker can generate audible sounds from signals derived from executing the test instructions. Good hearing test results have been achieved using headphone speakers.

The hearing test method 10 can generate the test sound in the proximity of a subject 80 and the subject 80 can generate a subject signal to indicate test sound audibility. In an embodiment, the subject 80 can wear headphones through which the test sound is generated. In another embodiment, the subject 80 is seated proximal a speaker and within a sound-insulated room. It can be useful to minimize ambient noise and environmental noise during the hearing test.

The subject 80 can generate the subject signal by selecting a region of a graphic user interface (GUI) with a computer pointing device, such as a mouse, track ball, and various other devices and combinations thereof. Alternatively, the subject 80 can generate the subject signal by activating a signaling device, such as a button, lever, touchpad, foot switch, sound-activated switch, and various other signaling devices and combinations thereof. Alternatively, the subject 80 can indicate test sound audibility to a tester, and the tester can generate the subject signal.

The hearing test method 10, via the computer processor 11, can detect 130 the subject signal and measure 140 a test elapsed time that can be a time period from starting executing the test instructions until the subject signal is detected 130.

The hearing test method 10, via the computer processor 11, can measure 140 a test elapsed time where the elapsed time is measured 140 from commencing executing 120 the test instructions until detecting 130 the subject signal indicating audibility of the test sound. For example, the hearing test method 10 via the computer processor 11 can store a start test time (t1) when executing the test instructions begins. The hearing test method 10 via the computer processor 11 can store a subject signal time (t2) when the subject signal is detected. The hearing test method 10, via the computer processor 11, can calculate a difference (t2−t1) between the start test time and the subject signal time and the test elapsed time can be the difference. Alternatively, the hearing test method 10 via the computer processor 11 can initiate an elapsed time counter when the sound generating system 121 begins to generate the test sound and then store directly the value of the elapsed time counter when the subject signal is detected 130. Alternatively, the hearing test method 10 via the computer processor 11 can measure 140 the test elapsed time in various other ways and combinations thereof.

The hearing test method 10 can transform 150 the test elapsed time via the computer processor 11 into a subject sound pressure level threshold that indicates a subject hearing sensitivity at the single audible frequency. The subject sound pressure level threshold can have units of sound pressure level (SPL) and can be converted to other units to facilitate comparison with various standardized values and specially developed values for evaluating subject hearing. Some commonly used values are equal-loudness contours such as Fletcher-Munson curves and Robinson-Dadson curves.

Transforming 150 the test elapsed time can occur by utilizing an algorithm, where the algorithm applies the pre-determined relationship to the test elapsed time in order to calculate a corresponding subject SPL threshold. Alternatively, transforming 150 can occur by searching a database of representative elapsed times and corresponding representative SPL's, selecting the representative elapsed time nearest the test elapsed time, and approximating the subject SPL threshold with the corresponding representative SPL. Transforming 150 can occur by various other modes and methods and combinations thereof.

The hearing test method 10 via the computer processor 11 can display 160 the subject SPL threshold for evaluating the subject hearing acuity. The hearing test method 10 can display 160 the subject SPL threshold on a graphic display 161 such as a computer monitor. Alternatively, the subject SPL threshold can be displayed 160 on various graphic displays such as printed on a printer, can be projected via a projector, and can be saved in digital format such as JPEG, BMP, TIFF and various other formats for subsequent viewing on a graphic display.

The subject SPL threshold can be displayed 160 as a graph showing the subject SPL threshold compared to the various standardized values and compared to the specially developed values for evaluating subject hearing.

Alternatively, the subject SPL threshold can be displayed 160 via an audio broadcast utilizing computer-generated vocalization of threshold values.

An embodiment of the hearing test method 10 can test hearing across a range of frequencies. The embodiment can read 110 a first test file from a first test file storage location. The first test file can comprise first instructions for causing a sound generating system 121 to generate 125 a first test sound. The first test sound can comprise a single tone at a first audible frequency.

The embodiment can read 110 a second test file from a second test file storage location. The second test file can comprise second instructions for causing the sound generating system 121 to generate 125 a second test sound. The second test sound can comprise a single tone at a second audible frequency.

The first test sound and the second test sound can comprise a changing first test volume amplitude and a changing second test volume amplitude, where the first test volume amplitude and the changing second test volume amplitude change according to pre-defined relationships between the first test volume amplitude and elapsed time and between the second test volume amplitude, respectively.

The embodiment can execute 120 the first test instructions and the second test instructions to cause the sound generating system 121 to generate 125 the first test sound and the second test sound, respectively.

The embodiment can detect 130 a first subject signal and can detect 130 a second subject signal indicating first test sound audibility and second test sound audibility, respectively.

The embodiment can measure 140 a first test elapsed time and a second test elapsed time.

The embodiment can transform 150 the first test elapsed time into a first subject SPL threshold at the first audible frequency using the pre-defined relationship between the first test volume amplitude and the first elapsed time. The embodiment can transform the second test elapsed time into a second SPL level threshold at the second audible frequency using the pre-defined relationship between the second test volume amplitude and the second elapsed time.

The embodiment can display 160 the first subject SPL threshold and the second subject SPL threshold via a graphic display.

Figure 3:
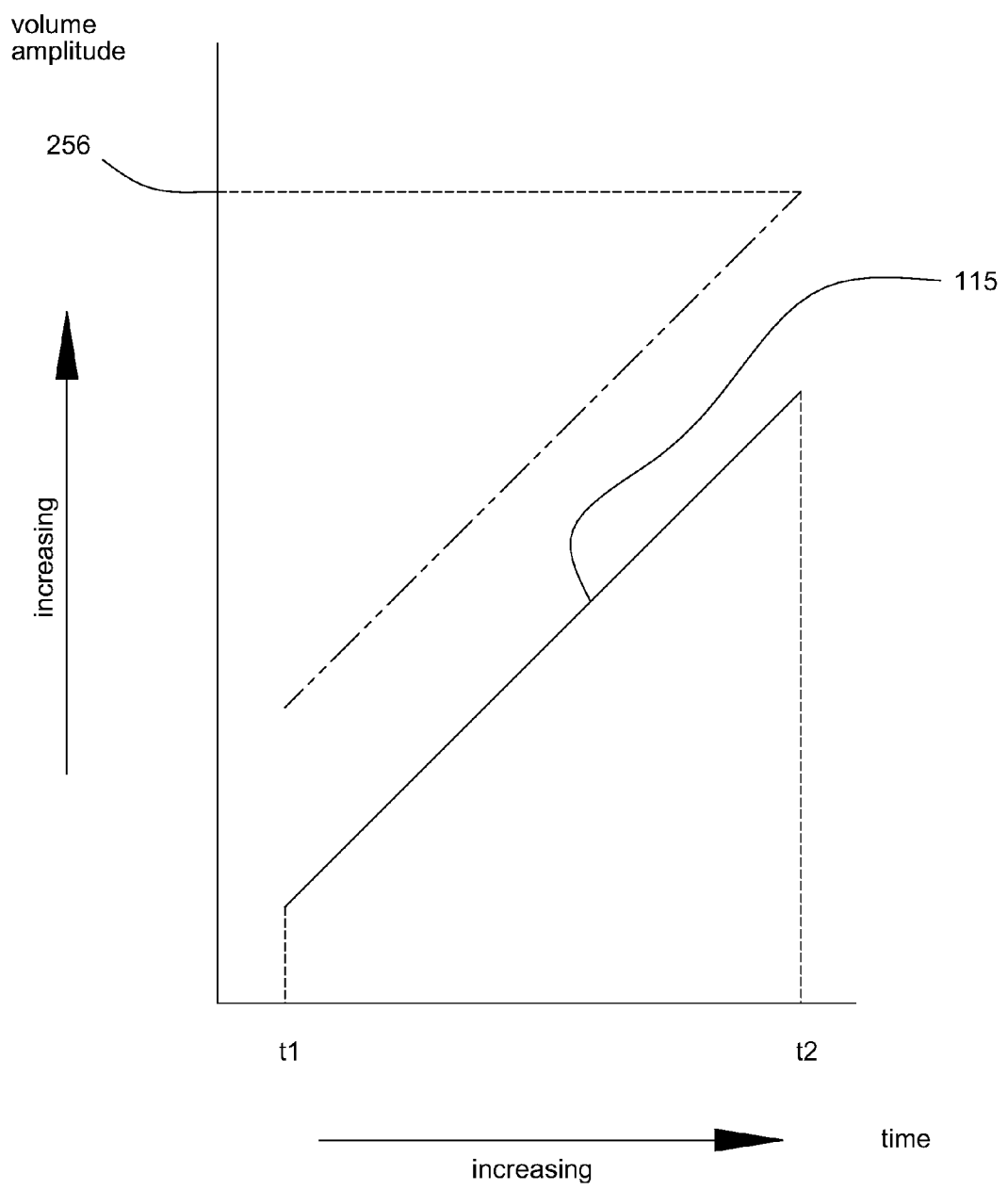
FIG. 3 is a diagram showing a test sound curve shifted to a compensated volume control setting.

As shown in FIG. 3, the hearing test method 10 can comprise a calibration procedure 20 for calibrating the sound generating system 121. Different sound generating systems can generate different sounds from the same instructions. Such differences can skew test results. The calibration procedure 20 can facilitate compensating for differences between sound generating systems so as to produce more accurate test results.

In an embodiment comprising the calibration procedure 20, the subject 80 can activate the calibration procedure 20 by selecting a region of a graphic user interface (GUI) with a computer pointing device, such as a mouse, track ball, and various other devices and combinations thereof. Alternatively, the subject 80 can activate the calibration procedure 20 by activating a signaling device, such as a button, lever, touch pad, foot switch, sound-activated switch, and various other signaling devices and combinations thereof. Alternatively, a tester can activate the calibration procedure 20.

The calibration procedure 20 can comprise reading 210 a pre-generated calibration file 211 from a calibration file storage location 2112. The calibration file 211 can comprise computer-executable calibration instructions for causing the sound generating system 121 to generate 225 a calibration sound. The calibration sound can be a single tone at a single audible frequency and can have a constant calibration volume amplitude.

The pre-generated calibration file 211 can comprise instructions in similar formats as the pre-generated test file 111 and can be read-only protected similarly to the pre-generated test file 111.

The calibration file storage location 212 can be a computer-readable medium such as a compact disk, a floppy disk, and a tape drive. The calibration file storage location 212 can be a hard disk drive, and can be a flash drive. The calibration file storage location 212 can be various volatile and non-volatile memory locations.

The calibration file storage location 212 can be accessed over a computer network including a wireless network and the Internet.

The hearing test method 10 can execute 220 the calibration instructions via the computer processor 11 to cause the sound generating system to generate 225 the calibration sound.

The hearing test method 10 can measure 230 the actual sound pressure level of the calibration sound generated by the sound generating system 121. Measuring 230 the actual SPL of the calibration sound can be done using an independent sound pressure level meter 231. An "independent sound pressure level meter" as used here and throughout means the meter measures actual sound pressure level of the calibration sound and is not responsive to instructions, signals, and settings that cause the sound generating system 121 to generate 225 the calibration sound. The independent sound pressure level meter 231 measures sound pressure level, that is, measures mechanical vibrations generated by the sound generating system 121. An example of an independent sound pressure level meter 231 is a hand-held dB meter such as is commonly used in recording studios, environmental studies, noise pollution evaluations, and various applications where sound pressure level measurements are required. Sound pressure level meters can operate via various principles and modes so long as they measure actual sound pressure level.

Measuring 230 the actual SPL of the calibration sound can give an indication of the characteristics of the sound generating system 121 and of the variance of the sound pressure level produced by the sound generating system 121 given instructions to produce the calibration sound at the calibration volume amplitude.

The hearing test method 10 can measure 240 a difference between the actual sound pressure level, as measured by the independent sound pressure level meter 231, and a predetermined target sound pressure level 241. The predetermined target SPL 241 can be prescribed by the method, can be selected from a range of recommended sound pressure levels, and can be assigned according to various sound generating system characteristics and subject characteristics such as age, historical data, and environmental conditions. The predetermined target SPL 241 can be the calibration volume amplitude.

In an embodiment comprising a calibration procedure 20, measuring 240 the difference between the actual SPL and the target SPL 241 can be performed by the subject. The subject 80 can read the measured actual SPL from the sound pressure level meter 231 and can adjust a sound generating system volume control until the measured actual SPL is within an acceptable range of the target SPL 241.

The hearing test method 10 can store 250 a calibration number 251 in a calibration number storage location 252. The calibration number 251 can be related to the measured difference between the actual SPL of the calibration sound and the predetermined target SPL 241. The calibration number 251 can be utilized to indicate the variance between the actual SPL of the calibration number and the calibration volume amplitude. In the aforementioned embodiment, the calibration number 251 can be related to the adjusting needed to achieve an actual SPL within the acceptable range of the target SPL.

For example, the predetermined target SPL 241 can be set by the hearing test method at 70 dB. When the measured actual SPL of the calibration sound is 60 dB, the subject can adjust the sound generating system volume control to a new, compensated volume control setting where the actual SPL measures 70 dB. The compensated volume control setting can be stored as the calibration number 251.

The subject can adjust the sound generating system volume and can store the calibration number 251 by selecting a region of a graphic user interface (GUI) with a computer pointing device, such as a mouse, track ball, and various other devices and combinations thereof. Alternatively, the subject 80 can adjust the sound generating system volume control and store the calibration number 251 by activating a signaling device, such as a button, lever, touchpad, foot switch, sound-activated switch, and various other signaling devices and combinations thereof. Alternatively, a tester can adjust the sound generating system volume control and store the calibration number 251.

An embodiment comprising the calibration procedure 20 can further comprise a test procedure 30. The test procedure 30 can utilize the calibration procedure 20 to compensate for differences between sound generating systems.

A test procedure 30 utilizing the calibration procedure 30 can read 110 the pre-generated test file 111 from the test file storage location 112. The test procedure 30 can read 255 the calibration number 251 from the calibration number storage location and adjust 270 the sound generating system 121 in accordance with the calibration number 251 to compensate for the measured difference between the actual sound pressure level of the calibration sound and the predetermined target sound pressure level 241. The test procedure 30 can execute 120 the test instructions and generate 125 the test sound.

As shown in FIG. 3, in another embodiment the calibration number 251 can be utilized as the maximum test volume amplitude for the test sound. For example, where the test sound can be represented as a continuous test sound curve 115 starting from a start test volume amplitude at the start test time (t1) and concluding with a stop test volume amplitude at the subject signal time (t2), the embodiment can adjust the sound generating system volume so that the stop test volume amplitude equals the calibration number 251. In this embodiment, the entire test sound curve is shifted up or down so that the pre-defined relationship between the test volume amplitude and elapsed time is preserved.

Alternatively, when the calibration number 251 equals a decibel (dB) level that is 10 dB above the calibration volume amplitude, the hearing test method 10 can adjust the sound generating system 121 to decrease the sound pressure level by 10 dB when generating 125 the test sound.

After adjusting the sound generating system volume, the test procedure 30 can proceed with the method steps as previously described.

When testing hearing across a range of audible frequencies, an embodiment of the hearing test method 10 can calibrate the sound generating system 121 across a range of audible frequencies by reading and executing multiple calibration files. For example, the embodiment can read 210 a first calibration file comprising instructions for a first calibration sound at a first audible frequency. The embodiment can perform the calibration procedure 20 and store 250 a first calibration number related to characteristics of the sound generating system 121 at the first audible frequency. The embodiment can then read 210 a second calibration file, repeat the calibration procedure 20, and store a second calibration number related to characteristics of the sound generating system 121 at a second audible frequency.

The first and second calibration numbers can be used to adjust the sound generating system volume setting while executing test instructions for the first audible frequency and the second audible frequency, respectively.

The invention can comprise a computer program product 300 for practicing the hearing test method. The program product can comprise at least one computer-readable medium 301 comprising computer-executable program code.

The program code, when executed, can provide a method for administering a hearing test, the method comprising the aforementioned reading 110 the test file 111 from the test file storage location 112; executing 120 the test instructions and causing 125 the sound generating system 121 to generate the test sound; detecting 130 the subject signal; measuring 140 the test elapsed time; transforming 150 the test elapsed time into a subject SPL threshold; and displaying 160 the subject SPL threshold.

An embodiment of the program product can comprise program code that provides a method comprising the calibration procedure 20 and comprising the test procedure 30.

Figure 4:
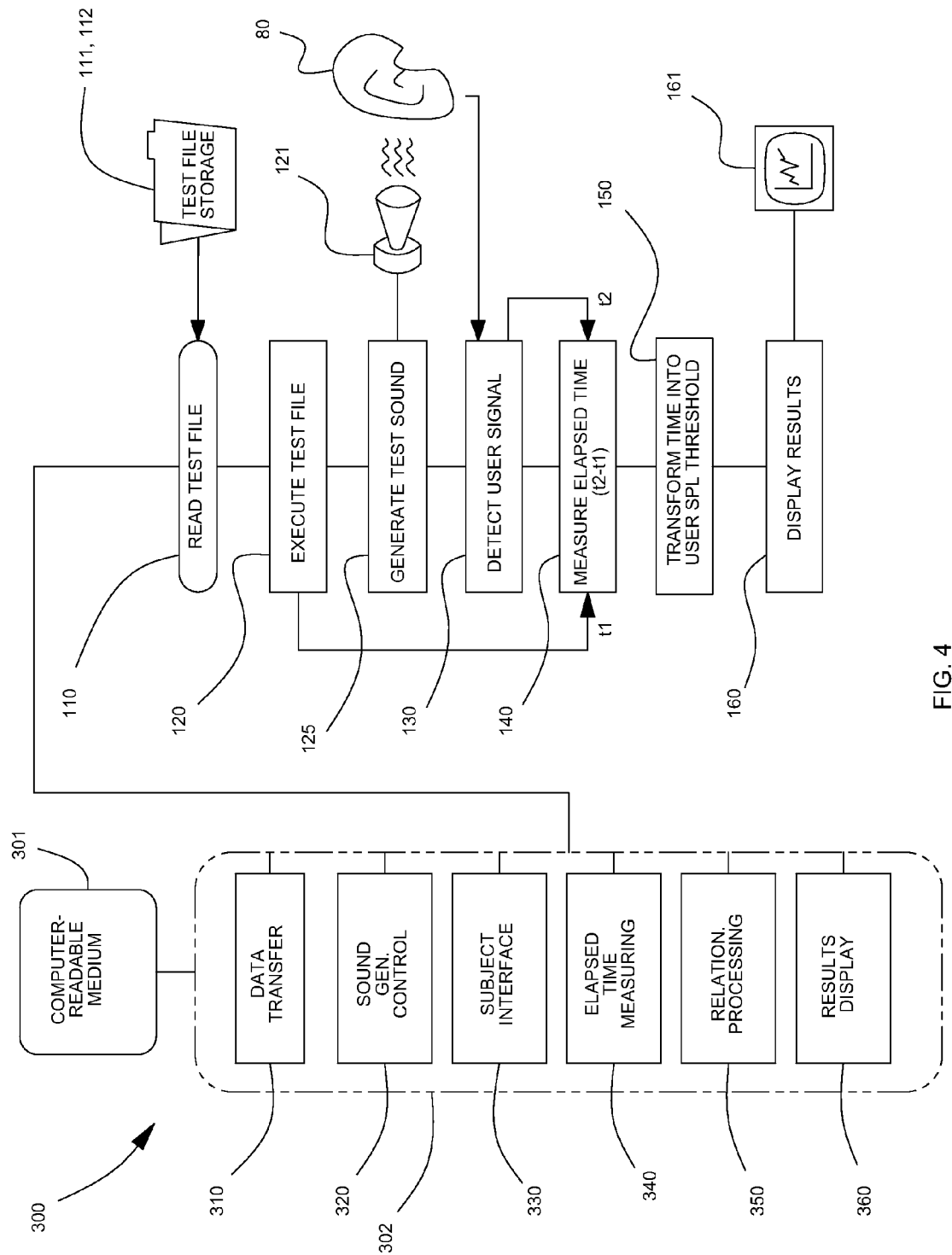
FIG. 4 is a diagram showing a computer program product embodiment practicing an embodiment of the hearing test method.

As shown in FIG. 4, an embodiment of the program product can include program code that comprises a method that provides a plurality 302 of program code groups for facilitating the method. For example, the method can provide the plurality 302 of program code groups including a subject interface group 330 that accepts subject input and that outputs information to the subject 80 including detecting the subject signal; a data transfer group 310 comprising instruction for reading data from storage locations and storing data in storage locations, and transferring data between code groups; a sound generating control group 320 comprising instructions for causing the sound generating system 121 to generate test sounds and calibration sounds, and for adjusting the sound generating system volume control; an elapsed time measuring group 340 comprising instructions to determine test elapsed time; a relationship processing group 350 comprising instructions to apply the pre-defined relationship to elapsed time received from the elapsed time measuring group 340 and transform the test elapsed time into a subject SPL threshold; and a results display group 360 comprising instructions for displaying the subject SPL threshold via various graphic displays.

The invention claimed is:

1. A hearing test method comprising:
   reading a pre-generated, read-only, test file via a computer processor from a test file storage location, the test file comprising:
      computer-executable test instructions for causing a sound generating system to generate a continuous test sound at changing test volume amplitude where the test volume amplitude changes according to a pre-defined relationship between the test volume amplitude and elapsed time, the test sound being a single tone at a single audible frequency;
   executing the computer-executable test instructions via the computer processor and causing the sound generating system to generate the test sound;
   detecting, via the computer processor, a subject signal that indicates test sound audibility;
   measuring, via the computer processor, a test elapsed time from executing the test instructions until detecting the subject signal;
   transforming the test elapsed time, via the computer processor, into a subject sound pressure level threshold at the single audible frequency using the pre-defined direct relationship between the test volume amplitude and the test elapsed time; and
   displaying the subject sound pressure level threshold via a graphic display device.

2. The hearing test method of claim 1 wherein the test volume amplitude changes by increasing according to a pre-defined direct relationship between the test volume amplitude and elapsed time.

3. The hearing test method of claim 2 wherein the pre-defined direct relationship between the test volume amplitude and elapsed time comprises:
   the increasing test volume amplitude increasing linearly with elapsed time from a starting test volume amplitude to a final test volume amplitude.

4. The hearing test method of claim 3 wherein transforming the test elapsed time into a subject sound pressure level comprises:
   multiplying a test volume amplitude linear increase rate per second by the test elapsed time measured in seconds.

5. The hearing test method of claim 2 wherein the final test volume amplitude causes the sound generating system to generate the test sound at a final test sound pressure level that is between 60 decibels and 90 decibels.

6. The hearing test method of claim 2 wherein displaying the subject sound pressure level threshold further comprises:
   comparing the subject sound pressure level threshold to a representative sound pressure level threshold of a theoretical average subject hearing the single tone at the single audible frequency.

7. The hearing test method of claim 2 wherein the increasing test volume amplitude is a continuously increasing test volume amplitude.

8. A hearing test method comprising:
   reading a pre-generated, read-only, first test file from a first test file storage location, the first test file comprising:
      computer-executable first instructions for causing a sound generating system to generate a continuous first test sound at an increasing first test volume amplitude where the first test volume amplitude increases according to a pre-defined direct relationship between the first test volume amplitude and elapsed time, the first test sound being a single tone at a first audible frequency;

executing the first instructions via a computer processor to cause the sound generating system to generate the first test sound;

detecting a first subject signal that indicates first test sound audibility;

measuring a first test elapsed time from executing the first test instructions until detecting the first subject signal;

transforming the first test elapsed time into a first subject sound pressure level threshold at the first audible frequency using the pre-defined direct relationship between the first test volume amplitude and the first test elapsed time;

reading a pre-generated, read-only, second test file from a second test file storage location, the second test file comprising:

computer-executable second instructions for causing a sound generating system to generate a continuous second test sound at an increasing second test volume amplitude where the second test volume amplitude increases according to a pre-defined direct relationship between the second test volume amplitude and elapsed time, the second test sound being a single tone at a second audible frequency;

executing the second instructions via a computer processor to cause the sound generating system to generate the second test sound;

detecting a second subject signal that indicates second test sound audibility;

measuring a second test elapsed time while executing the second test instructions until detecting the second subject signal;

transforming the second test elapsed time into a second subject sound pressure level threshold at the second audible frequency using the pre-defined direct relationship between the second test volume amplitude and the second test elapsed time;

displaying the first subject sound pressure level threshold and second subject sound pressure level threshold via a graphic display.

9. The hearing test method of claim 8 wherein the first pre-defined direct relationship between the first increasing test volume amplitude and elapsed time comprises:

the first increasing test volume amplitude increases linearly with elapsed time from a first starting test volume amplitude to a first final test volume amplitude;

wherein the second pre-defined direct relationship between the second increasing test volume amplitude and elapsed time comprises:

the second increasing test volume amplitude increases linearly with elapsed time from a second starting test volume amplitude to a second final test volume amplitude.

10. The hearing test method of claim 9 wherein transforming the first test elapsed time into a first subject sound pressure level comprises:

multiplying a first test volume amplitude linear increase rate per second by the first test elapsed time measured in seconds;

and wherein transforming the second test elapsed time into a second subject sound pressure level comprises:

multiplying a second test volume amplitude linear increase rate per second by the second test elapsed time measured in seconds.

11. The hearing test method of claim 8 wherein the first final test volume amplitude causes the sound generating system to generate the first test sound at a first final test sound pressure level that is between 60 and 90 decibels; and wherein the second final test volume amplitude causes the sound generating system to generate the second test sound at a second final test sound pressure level that is between 60 decibels and 90 decibels.

12. The hearing test method of claim 8 wherein displaying the first subject sound pressure level threshold and the second subject sound pressure level threshold further comprises:

comparing the first subject sound pressure level threshold and the second subject sound pressure level threshold to representative sound pressure level thresholds of a theoretical average subject hearing the single tone at the first and second audible frequencies, respectively.

13. A hearing test method comprising:

a calibration procedure comprising:

reading a pre-generated, read-only, calibration file from a calibration file storage location, the calibration file comprising:

computer-executable calibration instructions for causing a sound generating system to generate a calibration sound at a constant calibration volume amplitude, the calibration sound being a single tone at a single audible frequency;

executing the calibration instructions via a computer processor to cause the sound generating system to generate the calibration sound;

measuring with an independent sound pressure level meter an actual sound pressure level of the calibration sound generated by the sound generating system;

measuring a difference between the actual sound pressure level of the calibration sound and a predetermined target sound pressure level;

storing a calibration number in a calibration number storage location, where the calibration number is related to the difference between the actual sound pressure level generated by the sound generating system and the predetermined target sound pressure level;

a test procedure comprising:

reading a pre-generated, read-only, test file from a test file storage location, the test file comprising:

computer-executable test instructions for causing the sound generating system to generate a continuous test sound at increasing test volume amplitude where the test volume amplitude increases according to a pre-defined direct relationship between the test volume amplitude and elapsed time, the test sound being a single tone at the single audible frequency;

reading the calibration number from the calibration number storage location;

adjusting a sound generating system volume setting in accordance with the calibration number to compensate for the measured difference between the actual sound pressure level generated by the sound generating system and the predetermined target sound pressure level;

executing the test instructions via a computer processor to cause the sound generating system to generate the test sound;

detecting, via the computer processor, a subject signal that indicates test sound audibility;

measuring, via the computer processor, a test elapsed time while executing the test instructions until detecting the subject signal;

transforming the test elapsed time via the computer processor into a subject sound pressure level threshold at the single audible frequency using the pre-defined direct relationship between the test volume amplitude and the test elapsed time; and an output procedure comprising:
displaying the subject sound pressure level threshold via a graphic display.

14. The hearing test method of claim 13 where the calibration procedure further comprises:
adjusting the sound generating system volume control to a compensated volume control setting where the difference between the actual sound pressure level of the calibration sound is within a specified range of the predetermined target sound pressure level;
where the calibration number comprises the compensated volume control setting; and
where, in the testing procedure, adjusting the sound generating system volume setting in accordance with the calibration number comprises:
adjusting the sound generating system volume control to the compensated volume control setting.

15. The hearing test method of claim 13 where displaying the subject sound pressure level threshold further comprises:
comparing the subject sound pressure level threshold to a representative sound pressure level threshold of a theoretical average subject hearing the single tone at the single audible frequency.

16. A computer program product comprising:
at least one computer-readable medium comprising computer-executable program code embodied therein, the program code when executed providing a method for administering a hearing test, the method comprising:
a test procedure comprising:
reading a pre-generated, read-only, test file from a test file storage location, the test file comprising: computer-executable test instructions for causing a sound generating system to generate a continuous test sound at increasing test volume amplitude where the test volume amplitude increases according to a pre-defined direct relationship between the test volume amplitude and elapsed time, the test sound being a single tone at the single audible frequency;
executing the test instructions and causing the sound generating system to generate the test sound;
detecting a subject signal where the subject signal indicates test sound audibility;
measuring a test elapsed time from executing the test instructions until detecting the subject signal;
transforming the test elapsed time into a subject sound pressure level threshold at the single audible frequency by applying the pre-defined direct relationship between the test volume amplitude and the test elapsed time; and
an output procedure comprising:
displaying the subject sound pressure level threshold on a graphic display device.

17. The computer program product of claim 16 where the method for administering a hearing test further comprises:
providing a plurality of program code groups including:
a subject interface group that accepts subject input and that displays program output;
a data transfer group;
a sound generating control group;
an elapsed time measuring group;
a relationship processing group programmed to apply the pre-defined relationship to data received from the elapsed time measuring group;
a results display group;

where the test procedure further comprises:
reading a pre-generated, read-only, test file from a test file storage location via the data transfer group, the test file comprising: computer-executable test instructions for causing a sound generating system to generate a continuous test sound at increasing test volume amplitude where the test volume amplitude increases according to a pre-defined direct relationship between the test volume amplitude and elapsed time, the test sound being a single tone at the single audible frequency;
executing the test instructions via the sound generating control group and causing the sound generating system to generate the test sound;
detecting a subject signal via the subject interface group where the subject signal indicates test sound audibility;
measuring a test elapsed time, via the elapsed time measuring group, from executing the test instructions until detecting the subject signal;
transforming the test elapsed time into a subject sound pressure level threshold at the single audible frequency, via the relationship processing group, by applying the pre-defined direct relationship between the test volume amplitude and the test elapsed time; and
where the output procedure further comprises:
displaying the subject sound pressure level threshold, via the results display group, on a graphic display device.

18. The computer program product of claim 17 wherein method for administering a hearing test further comprises:
a calibration procedure comprising:
reading a pre-generated, read-only, calibration file from a calibration file storage location via the data transfer group, the calibration file comprising:
computer-executable calibration instructions for causing the sound generating system to generate a continuous calibration sound at a constant calibration volume amplitude, the calibration sound being a single tone at the single audible frequency;
executing the calibration instructions via the sound generating control group and causing the sound generating system to generate the calibration sound;
measuring with an independent sound pressure level meter an actual sound pressure level of the calibration sound generated by the sound generating system;
measuring a difference between the actual sound pressure level of the calibration sound and a predetermined target sound pressure level;
storing a calibration number, via the data transfer group, in a calibration number storage location, where the calibration number is related the difference between the actual sound pressure level generated by the sound generating system and the predetermined target sound pressure level;
wherein the test procedure further comprises:
prior to executing the test instructions, reading the calibration number, via the data transfer group, from the calibration number storage location; and
adjusting a sound generating system volume setting in accordance with the calibration number to compensate for the measured difference between the actual sound pressure level generated by the sound generating system and the predetermined target sound pressure level.

19. The computer program product of claim 18 wherein the calibration procedure further comprises:
  adjusting the sound generating system volume control to a compensated volume control setting where the difference between the actual sound pressure level of the calibration sound is within a specified range of the predetermined target sound pressure level;
  where the calibration number comprises the compensated volume control setting; and
  where, in the testing procedure, adjusting the sound generating system volume setting in accordance with the calibration number comprises:
    adjusting the sound generating system volume control to the compensated volume control setting.

20. The computer program product of claim 16 where displaying the subject sound pressure level threshold further comprises:
  displaying a visual comparison of the subject sound pressure level threshold to a representative sound pressure level threshold of a theoretical average subject hearing the single tone at the single audible frequency.

* * * * *